United States Patent [19]
Kiefer

[11] Patent Number: 4,708,835
[45] Date of Patent: Nov. 24, 1987

[54] METHOD AND APPARATUS FOR MAKING A DENTAL MODEL MOUNTED ON A BASE PLATE

[76] Inventor: Wilhelm H. Kiefer, Obere Mühlstrasse 8, D-7520 Bruchsal 4, Fed. Rep. of Germany

[21] Appl. No.: 781,955

[22] Filed: Sep. 30, 1985

[30] Foreign Application Priority Data

Oct. 2, 1984 [DE] Fed. Rep. of Germany ....... 3436094

[51] Int. Cl.$^4$ ...................... A61C 13/08; A61C 13/10
[52] U.S. Cl. ........................................ 264/17; 433/74; 433/213
[58] Field of Search ...................... 264/16, 17; 249/54; 433/213, 74

[56] References Cited

U.S. PATENT DOCUMENTS

| | | | |
|---|---|---|---|
| 2,842,845 | 7/1958 | Carlson | 433/74 |
| 4,021,916 | 5/1977 | Spalten | 433/74 |
| 4,371,339 | 2/1983 | Feiser | 433/74 |
| 4,439,151 | 3/1984 | Whelan | 433/74 |

FOREIGN PATENT DOCUMENTS 1566194 8/1970 Fed. Rep. of Germany .
2653743 6/1978 Fed. Rep. of Germany .

*Primary Examiner*—Jan H. Silbaugh
*Assistant Examiner*—Karen D. Kutach
*Attorney, Agent, or Firm*—Frishauf, Holtz, Goodman & Woodward

[57] ABSTRACT

A method and apparatus for making a model of a set of teeth, in which each tooth is mounted on a holding pin (17) which is removably disposed in a base plate (15). For positioning of the holding pins, a datum plate (10) of transparent material is placed on the impression (5) of a jaw and the desired positions, of a respective holding pin for each tooth root, are marked. Then pins are inserted into a pre-perforated base plate (15) according to the markings, or a pre-perforated base plate of transparent material is used instead of the transparent datum plate (10), and is marked with desired pin positions on one side and provided with pins on its other side. The pins then penetrate molding material placed in the impression (5), and harden in place as the molding material hardens. The hardened molded material can then be sawed into separate parts.

19 Claims, 4 Drawing Figures

METHOD AND APPARATUS FOR MAKING A DENTAL MODEL MOUNTED ON A BASE PLATE

The present invention relates generally to a method and apparatus for producing dental models with individually removable teeth, and more particularly to a labor-saving method and apparatus for positioning the respective pins which support each tooth in the model's base plate.

BACKGROUND

Dental models, in which the individual teeth can be removed, are needed for producing crowns, bridges, and tooth prostheses. In order to form such replacement parts to fit precisely into the model, the model parts must be made removable, which means that, after sawing apart the originally cast model, the model parts must each be mounted on a folded pin which fits into a base plate. Starting from the original jaw impression used to cast the model, the process of correctly positioning the holding pins, whose locations differ as widely as the positions of a particular tooth in different people's jaws, for the respective models, has heretofore been very labor-intensive.

For mounting these pins, one has heretofore used so-called pin sets. These have an X-Y movable stage on whose upper side is disposed the receptacle containing the jaw impression, and whose lower side supports the base plate. A fixed datum or alignment or sounding shaft is located above the jaw impression and corresponds to a fixed drill located under the base plate and having a shank which is aligned with the shank of the sounding shaft. The X-Y movable stage is moved around in such a way that the sounding shaft is directed to the positions where one wishes to later place a pin for mounting a model part. Upon reaching the desred positions, the X-Y movable stage is depressed, so that the drill makes a corresponding hole in the base plate. This process must be painstakingly repeated a number of times corresponding to the number of removable parts needed in the model. Conventionally, each tooth root or removable part in the models requires two pins, so that the part can not rotate when mounted in the base plate.

Finally, pins are inserted into the finished, perforated base plate, the jaw impression is filled with plaster or similar molding material, and the base plate with protruding pins is lowered onto the molding material, taking care that the base plate is exactly aligned, so that where the pins actually penetrate the plaster or other molding material is at the desired positions.

The disadvantages of this conventional procedure are, first of all, that the pin sets are very expensive. Aside from that, during drilling it often happens that the stage moves or the base plate becomes canted, so that the relatively thin drilling bit breaks off. Beyond that, the required procedure with the conventional pin sets is relatively involved, and the precisely undertaken feeling-out of the positions for the pins sometimes comes to naught, because the alignment of the pin-equipped base plate over the jaw impression filled with molding material requires a very precise eye. Finally, the time required for the conventional procedure is very high.

THE INVENTION

Accordingly, it is an object of the invention to improve and simplify the method and apparatus conventionally used for positioning the pins on the base plate, so that the need for expensive machines is avoided, the worktime is substantially reduced, and the desired precision in pin positioning is achieved without the danger of disturbances during the work process.

Briefly, a datum or sounding plate of transparent material is placed on the impression in such a way that the desired positions of the holding pins can be marked on the side of the datum plate remote from the impression, the base plate is pre-perforated with a field of closely spaced holes in the curved region over the jaw impression, the datum plate is flipped over in a guide means, the base plate is laid in the guide means against the side of the datum plate remote from the markings, and holding pins are inserted in the base plate corresponding to the markings on the datum plate.

Due to the features of the present invention, it is possible to very quickly mark, on the preferably glass-clear datum plate, the positions at which the base plate should be provided with pins. Thereafter, the datum plate is simply flipped over, and, by means of a common guide means, the base plate is placed atop it in precise alignment. The base plate has been pre-perforated at the time of its manufacture with an array of holes. Upon looking through the holes, one can see the markings made on the datum plate and place in the base plate the corresponding pins. Since the pins must be inserted from the side of the base plate remote from the datum plate, the datum plate had to be first flipped over, so that a pin pattern mirror-reversed from the pattern of the filled-in impression does not result.

In a variation of the method and apparatus of the invention, a transparent base plate is provided, having a field of closely spaced holes in the region of the impression. The base plate is laid over the impression in a guide means, and the desired positions of the pins are marked on the side of the base plate remote from the impression. The base plate is flipped over in the guide means, and holding pins are inserted on the side which was adjacent to the impression, i.e. the side opposite to the side bearing the markings. This is a further simplification from the embodiment first described, which featured both a base plate and a datum plate. Again, it is advantageous to make the base plate glass-clear and transparent, so that the desired positions of the pins can be marked on the side remote from the impression, and one can, by simply flipping over the base plate, see the positions where the pins should be inserted. In order to avoid the individual drilling of the holes, it is again advantageous to make the base plate pre-perforated with a field of holes, from which one can simply select the appropriate ones in accordance with the markings.

Both versions of the invention are exceptionally simple and reliable in their operation. In particular, no additional machines are necessary for carrying them out. In view of the fact that the plates used are each guided with respect to the impression, there is no difficulty in correctly placing the finished base plate on the molding material in the impression. Errors and inaccuracies cannot occur.

As for the marking of the pin positions, this can be accomplished by sticking marker pins in the corresponding holes in the datum plate which can be provided with a field of closely spaced/adjacent holes. The marking of the holding pin positions could also be done by making colored points or the like.

In accordance with the first version of the invention, the apparatus adapted for practicing it can advantageously be formed as follows: a datum plate, similar to the base plate and made of transparent material, is placed on the impression. The datum plate has a filled of closely spaced/adjacent holes. The datum plate is held in proper registration over the impression by a guide means, and the base plate is held in proper registration over the impression by the same guide means. The base plate has, for the holding pins, a field of closely spaced/adjacent holes corresponding to that of the datum plate. The fields of holes of the datum plate and base plate are mirror-symmetric to an axis passing through the middle of the guide means.

With reference to this apparatus, its simplicity and reliability of operation must once again be stressed. Also, there are no special costs since the datum plate can be used repeatedly and a base plate is conventionally needed anyway for construction of the model. As for the mirror symmetry of the fields of holes of the datum plate and base plate, this permits the holes of the two plates to always be aligned, whenever the two plates are disposed in the common guide means.

With reference to the second version of the invention, the apparatus for practicing it is advantageously configured as follows: the base plate is of transparent material; it has for the pins a field of closely spaced/adjacent holes in the region of the impression; and it is held in its position on the impression in proper registration. Thus, all one requires is the already necessary base plate, in a correspondingly prepared state. The proper registration of the base plate on the impression is accomplished as follows: after the marking of the holding pin positions, the base plate is taken off the guide means in order to emplace the pins on the side of the plate adjacent to the impression; then, when the plate is re-seated in the guide means, it is returned to exactly the same position as when it was being marked, assuring that the now-emplaced pins are arranged exacly on the previously desired positions.

In the apparatus for practicing the second version of the invention, it can be advantageous to form the holes for the pins as "blind holes" open to only one side of the plate. This is particularly recommended when the marking is under taken by means of color points. The configuration of the holes as blind holes thus avoids any running of the color or ink into the holes. In order to simplify handling, the plate can be formed, on the side opposite that having the blind holes, with corresponding depressions or recesses, in which the color points can be precisely put or other marking means fastened.

For all of the above versions and embodiments, it can be advantageous for the holes and at least the longitudinal portions of the pins which fit into the holes, to have a common asymmetrical cross-section. This permits the use of only one pin for each tooth root, while the turning of the tooth root with respect to the base plate is nevertheless prevented. This not only cuts in half the work of marking the pin positions and emplacing the pins, it also saves half the pins and avoids the jamming which two pins of the same root may cause due to plaster expansion during hardening. This makes later handling easier.

It is further advantageous to make the longitudinal, to-be-inserted portions of the pins conical, so that good seating of the pins in the base plate results.

It is also advantageous to secure the jaw impression on a carrier plate which has an integral guide means. Such a guide means can be formed as a wall portion of the carrier plate projecting perpendicularly to the surface of the impression and having therein at least one guide slot for engagement with a matching guide tab of the datum plate and/or base plate.

These features assure, in particular, that during the entire handling, the guidance for the plates is always the same and their relative position to the jaw impression is preserved, so that during handling no errors or inaccuracies can arise.

DRAWINGS

Further features and details of the invention will be evident from the following description of preferred embodiments, as shown in the drawings, simplified and schematically illustrated, wherein.

DETAILED DESCRIPTION

Figure 1:
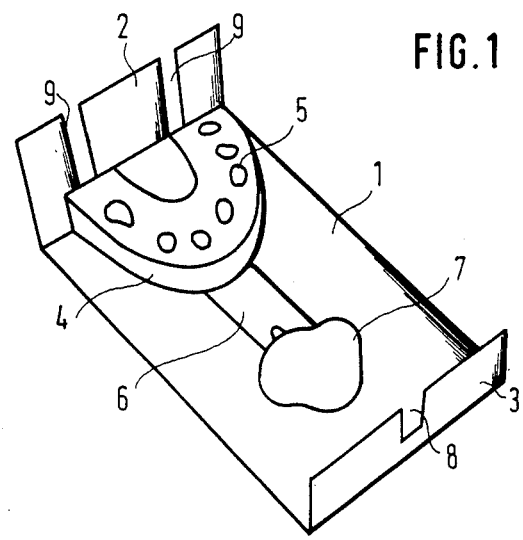
FIG. 1 is a perspective view of the carrier plate of the present invention with a dental impression fastened thereon.

FIG. 1 illustrates a generally rectangular carrier plate 1 with two orthogonally upwardly projecting wall portions 2 and 3 at opposite ends of the plate. An impression 5, of the teeth of an upper or lower jar, located in a receptacle 4, is fastened to the upper surface of the plate 1. The receptacle 4 abuts the wall portion 2 of the plate 1, and the handle 6 of the receptacle 4 is fixed to the plate 1 by a glob of silicone rubber 7. Alternatively, the handle 6 can be formed to engage a slot 8 in the wall portion 3 of the plate.

The wall portion 2 is formed with two guide slots 9, which preferably extend perpendicularly to the upper surface of the impression 5.

Figure 2:
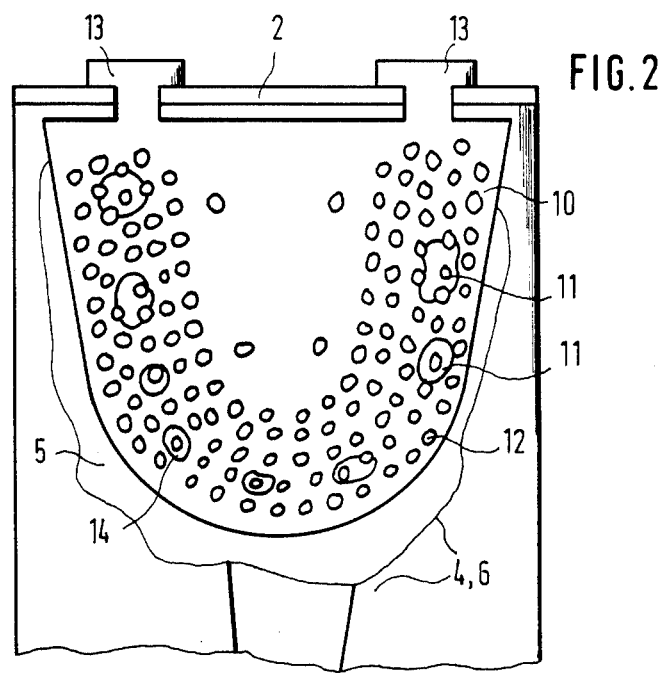
FIG. 2 is an enlarged, fragmentary top view of the carrier plate and impression of FIG. 1, with a transparent datum plate placed on top of the impression.

FIG. 2 is an enlarged plan or top view of the impression 5 of FIG. 1. A datum plate 10, preferably of transparent material, has been placed over the surface of the impression 5. Through the plate 10 one can see the contours 11 of the jaw impression. The plate 10 is provided, in the semi-circular region of the tooth impressions, with a field or array of closely spaced or adjacent holes 12. Further, the datum plate 10 is also provided with guide tabs 13, preferably T-shaped, which interfit securely with the guide slots 9 in wall portion 2 of carrier plate 1.

The fact that the contours of the impression 5 can be seen through the datum plate 10 makes it possible to mark the locations at which a base plate 15 later can be provided with pins. For example, marker pins 16 (FIG. 3) can be placed into holes 12 from the top, e.g. at the location identified by numeral 14 in FIG. 2.

Figure 3:
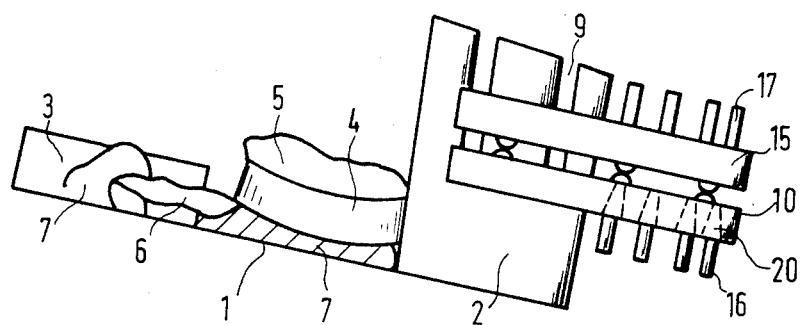
FIG. 3 is a schematic perspective view of the carrier plate of FIG. 1, taken from the opposite end and from a lower angle, showing the datum plate of FIG. 2 rotated 180°, placed next to a base plate, and provided with pin inserts.

A datum plate 10 provided with marking pins at these locations has a pin configuration which is the mirror image of the pin configuration actually required for the base plate 15. In order to reverse this mirror image, the datum plate 10 is flipped over and re-inserted in the guide slots 9, as shown in FIG. 3. Into these same guide slots 9, a similarly formed base plate 15, also having a semi-circular field of holes, is placed, so that it rests on the side of the datum plate 10 remote from the marker pins 16. One can then place holding pins 17 into the holes 18 of base plate 15 which are aligned with the marker pins 16 of datum plate 10. When one then removes both plates 10 and 15 from the guide slots 9, flips base plate 15 over, and re-inserts it in slots 9, the positions of the holding pins 17 with respect to the depressions in the impression 5 correspond exactly to the positions which were selected in FIG. 2 with the help of the datum plate 10.

Figure 4:
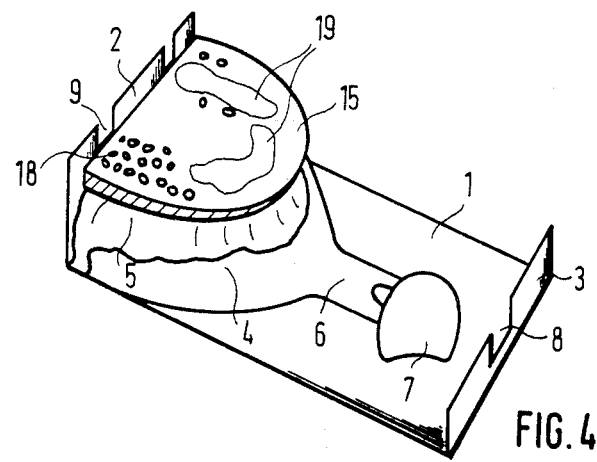
FIG. 4 is a perspective view similar to that of FIG. 1, with the finished base plate placed on the dental impression.

The base plate 15 may also comprise transparent material. This is not necessary, since one can see through the holes 18 in the base plate 15 the positions at which the corresponding holes 12 of the datum plate 10 have been closed by the insertion of marker pins 16. One can then insert holding pins 17 in the base plate 15 at corresponding positions. When one then flips over the base plate 15 thus prepared and puts it in position on top of the impression, with the help of the guide means 9, the positions of the pins 17 correspond exactly to the positions which were selected, as shown in FIG. 2, with the help of the datum plate 10. One can then fill the impression 5 with plaster and press the base plate 5, together with its pins 17, onto the plaster, so that the pins 17 dip into the plaster at the desired locations and become fixed there as the plaster hardens. This is illustrated in FIG. 4, in which the holes 18 of the base plate 15 are visible. Excess plaster, which runs out through the unused holes 18 as the base plate 15 is pressed down, is designated by reference numeral 19.

FIG. 3 shows that the pins 16 fit into conically shaped holes 20 in the datum plate 10. Pins 17 fit into similar conically shaped holes in base plate 15. One can form the pins and holes with non-round but corresponding or matching cross-sections, so that the pins will not rotate in the holes, and each tooth of the model will be prevented from rotating on the base plate, even though only one pin per tooth is provided.

FIG. 2 shows that one could insert pins in a base plate in the desired manner without using a datum plate as an intermediate element. For this purpose, one uses a base plate, of transparent material, corresponding to the plate 10, and having a field of holes 12. This plate is laid on the jaw impression 5 as shown in FIG. 2. The positions designated for later insertion of pins can be marked on the upper surface by insertion of corresponding pins or by making color markings on the plate. Now the plate is flipped over, so that pins can be placed on the other side. Thereafter, the impression 5 is filled with plaster or similar molding material and the plate is placed on top in the manner shown in FIG. 2, so that it acts as base plate and pins pressing into the plaster. Due to the conically formed pins and the matching, unround cross-sections of their holes, the advantage set forth above are achieved.

Insofar as one wishes, when using a transparent plate as a base plate, to mark it with inked or colored points, it is advantageous to form the holes on the impression-adjacent side as blind holes, so that, upon marking, the ink or coloring cannot run into the holes. For precision of marking, depressions or recesses can be provided on the plate side to be marked, corresponding to the blind holes on the opposite side of the plate.

As those skilled in the art will appreciate, various changes and modifications are possible within the scope of the inventive concept.

I claim:

1. Method of producing a dental model, with individually removable teeth, mounted on a flat base plate (15), by filling a dental impression (5), mounted on a carrier plate (1) having guide means (9), with hardenable molding material, including
    inserting holding pins, one end of each holding pin (17) corresponding to each tooth, tooth stump, or missing tooth into the unhardened molding material with the other end of the pin disposed in a hole (18) in the base plate,
    comprising the steps of:
    placing a transparent datum plate (10) over the impression (5) in said guide means (9),
    marking the desired positions of said holding pins (17) on the side of the datum plate (10) remote from the impression (5),
    providing the base plate (15) with a field of closely adjacent holes (18),
    flipping the datum plate (10) over in said guide means (9),
    placing said base plate (15) over the marking-remote side of the datum plate (10), and
    inserting said holding pins (17) in said base plate (15) at positions corresponding to the markings on the datum plate (10).
2. The method of claim 1,
    including providing the datum plate with a field of closely adjacent holes; and
    wherein the step of marking the datum plate comprises
    placing marker pins (16) in holes which are aligned with the desired positions of the holding pins (17).
3. The method of claim 1, wherein the desired positions of the holding pins (17) are marked using marker pins (16).
4. The method of claim 1, wherein the desired positions of the holding pins (17) are marked with color points.
5. The method of claim 2, wherein the desired positions of the holding pins (17) are marked with color points.
6. Method of producing a dental model, with individually removable teeth, mounted on a flat base plate (15), by filling a dental impression (5), mounted on a carrier plate (1) having guide means (9), with hardenable molding material, including
    inserting holding pins (17), one end of each holding pin corresponding to each tooth, tooth stump, or missing tooth into the unhardened molding material with the other end of the pin disposed in a hole (18) in the base plate,
    comprising the steps of:
    providing a transparent base plate (15) with a field of closely adjacent holes (18),
    placing the base plate (15) over the impression (5) in said guide means (9),
    marking the desired positions of said holding pins (17) on the side of the base plate (15) remote from the impression (5),
    flipping the base plate (15) over in said guide means (9), and
    inserting said holding/pins (17) in said base plate (15) on the impression-adjacent side thereof, at positions corresponding to the markings on the base plate (15).
7. The method of claim 6, wherein the desired positions of the holding pins (17) are marked with color points.

8. The method of claim 6, wherein the step of providing the transparent base plate (15) with the field of closely adjacent holes (18) comprises forming said holes as blind holes extending from the side of the base plate close to or facing the impression (5);

and the step of marking the desired positions of said holding pins (17) comprises marking the base plate with color points in alignment with said blind holes on the side of the base plate (15) remote from the impression (5).

9. Dental model making apparatus to provide a dental model with individually removable teeth by filling a dental impression (5) having depressions corresponding to each tooth, tooth stump or missing tooth with a hardenable molding material in which a holding pin (17) is to be inserted, said apparatus being utilized in carrying out the method of claim 1, and comprising a carrier plate (1), the impression (5) being secured to said carrier plate;

a datum plate (10) of transparent material and being formed with a field of closely paced holes (12);

guide means (9) secured to said carrier plate and guiding the position of the datum plate (10) with respect to the impression (5);

a plurality of marker pins (16) for placement in selected ones of said holes (12) to mark a tooth, tooth stump or missing tooth on said datum plate while maintaining proper registration with the impression (5);

a base plate (15) engageable with said guide means for guiding the position of said base plate (15) with respect to said impression and to said datum plate (10), said base plate being formed with a field of closely spaced holes (18) corresponding to and in alignment with the holes (12) in said datum plate when said base plate is located in said guide means adjacent said datum plate;

wherein the respective fields of holes (12, 18) of said datum plate (10) and of said base plate (15) are each mirror symmetrical about an axis through the middle of said guide means (9); and holding pins (17) located in selected ones of the closely spaced holes (18) of the base plate (15) corresponding to the position of marker pins (16) located in the holes (12) of the datum plate (10).

10. The apparatus of claim 9, wherein at least part of the holes (18) formed in the base plate (15) and at least a portion of the holding pins (17) have non-symmetrical cross section to prevent rotation of the pins in the holes and subsequent rotation of a tooth impression upon hardening of impression material about the holding pin.

11. The apparatus of claim 9, wherein at least a portion of the holes (18) in the base plate (15) and of the receiving pins (17) are cone-shaped.

12. The apparatus of claim 9, wherein said carrier plate is formed with a wall portion extending essentially perpendicularly to the surface of said impression (5);

a guide slot (9) formed in said wall portion;

and a guide tab (13) formed on said datum plate (10) and a further guide tab formed on said base plate (15), at least part of said wall portion, said guide slot and said guide tabs forming said guide means.

13. Dental model making apparatus to provide a dental model with individually removable teeth by filling a dental impression (5) having depressions corresponding to each tooth, tooth stump or missing tooth with a hardenable molding material in which a holding pin (17) is to be inserted, said apparatus being utilized in carrying out the method of claim 6, and comprising a carrier plate (1), the impression (5) being secured to said carrier plate;

a base plate (15) comprising transparent material, said base plate being formed with a field of closely spaced holes (18);

guide means (9) secured to said carrier plate and guiding the position of said base plate with respect to the impression (5);

marker points for placement on said transparent base plate and in registration with said spaced holes (18) and with at least one selected tooth, tooth stump or missing tooth on said impression, while maintaining proper registration with said impression;

wherein the respective field of holes of said base plate is mirror-symmetrical about an axis through the middle of said guide means to permit guidance of said base plate with either side of the base plate facing the impression.

14. The apparatus of claim 13, wherein said holes (18) to receive said holding pins (17) are formed as blind holes open at only one end.

15. The apparatus of claim 14, wherein said marker points comprise recesses formed on the side opposite said blind holes (18) on the base plate (15) and in alignment with and corresponding to said blind holes.

16. The apparatus of claim 14, wherein said carrier plate (1) is formed with a wall portion extending essentially perpendicularly to the surface of said impression (5);

a guide slot (9) is formed in said wall portion;

and a guide tab (13) is formed on said datum plate (10) and a further guide tab formed on said base plate (15), at least part of said wall portion, said guide slot and said guide tabs forming said guide means.

17. The apparatus of claim 13, wherein at least part of the holes (18) formed in the base plate (15) and at least a portion of the holding pins (17) have non-symmetrical cross setion to prevent rotation of the pins in the holes and subsequent rotation of a tooth impression upon hardening of impression material about the holding pin.

18. The apparatus of claim 13, wherein at least a portion of the holes (18) in the base plate (15) and of the receiving pins (17) are cone-shaped.

19. The apparatus of claim 13, wherein said carrier plate (1) is formed with a wall portion extending essentially perpendicularly to the surface of said impression (5);

a guide slot (9) is formed in said wall portion;

and a guide tab (13) is formed on said base plate (15), at least part of said wall portion, said guide slot and said guide tab forming said guide means.

* * * * *